United States Patent [19]
Hayakawa et al.

[11] Patent Number: 5,194,135
[45] Date of Patent: Mar. 16, 1993

[54] AIR/FUEL RATIO SENSOR

[75] Inventors: Nobuhiro Hayakawa; Ken Minoha; Yutaka Adachi; Haruhisa Shiomi, all of Aichi, Japan

[73] Assignees: NGK Spark Plug Co., Ltd., Aichi; Mitsubishi Denki K.K., Tokyo, both of Japan

[21] Appl. No.: 228,808

[22] Filed: Jul. 29, 1988

Related U.S. Application Data

[63] Continuation of Ser. No. 832,800, Feb. 25, 1986.

[30] Foreign Application Priority Data

Feb. 25, 1985 [JP] Japan .................................. 60-36032

[51] Int. Cl.$^5$ ..................... G01N 27/41; G01N 27/409
[52] U.S. Cl. ..................... 204/425; 204/426; 204/427
[58] Field of Search ............ 204/15, 421-429, 204/153.18

[56] References Cited

U.S. PATENT DOCUMENTS

| | | | |
|---|---|---|---|
| 4,294,679 | 10/1981 | Maurer et al. | |
| 4,502,939 | 3/1985 | Holfelder et al. | 204/425 |
| 4,505,806 | 3/1985 | Yamada | 204/425 |
| 4,505,807 | 3/1985 | Yamada | 204/425 |
| 4,568,443 | 2/1986 | Asayama et al. | 204/425 |
| 4,591,421 | 5/1986 | Yamada et al. | 204/425 |
| 4,610,741 | 9/1986 | Mase et al. | 204/424 |
| 4,769,123 | 9/1988 | Mase et al. | 204/426 |

FOREIGN PATENT DOCUMENTS 140028  3/1979  Norway ............................ 204/400

Primary Examiner—T. Tung
Attorney, Agent, or Firm—Sughrue, Mion, Zinn, Macpeak & Seas

[57] ABSTRACT

An air/fuel ratio sensor is described, comprising an oxygen concentration electrochemical cell and an oxygen pump disposed in a face-to-face relationship with a gap being formed therebetween, the side of said electrochemical cell opposite the side facing said oxygen pump being in contact with the atmosphere, said gap forming a gas diffusion compartment that communicates with a gas to be analyzed by a gas diffusion limiting means, wherein the gap existing between said oxygen concentration electrochemical cell and said oxygen pump has a width of no more than 0.22 mm and no less than 0.01 mm.

2 Claims, 5 Drawing Sheets

AIR/FUEL RATIO SENSOR

This is a continuation of application Ser. No. 832,800 filed Feb. 25, 1986.

BACKGROUND OF THE INVENTION

The present invention relates to an air/fuel (A/F) ratio sensor for detecting the A/F ratio of an air/fuel mixture being supplied into a combustor. More particularly, the present invention relates to an A/F ratio sensor that is capable of detecting the A/F ratio of an air/fuel mixture using an oxygen ion conductive solid electrolyte over the full operating range, including the lean region (where air is in excess of the stoichiometric value) to the rich region (where fuel is in excess of the stoichiometric value).

With a view to improving fuel economy and reducing emissions, some conventional combustors such as internal combustion engines, have been provided with the capability of feedback control, involving the detection of oxygen levels in the exhaust and control of the air/fuel mixture in the combustion chamber so as to burn it at an A/F ratio in the vicinity of the stoichiometric value. An oxygen sensor commonly used to detect the concentration of oxygen in the exhaust employs an ion conductive solid electrolyte with coatings of porous electrode layers and detects the burning of fuel at an A/F ratio in the vicinity of the stoichiometric value, depending upon the change in the electromotive force generated by the difference between the oxygen partial pressure of the exhaust and that of air. Generally, this type of oxygen sensor produces an output voltage that changes abruptly at the stoichiometric A/F ratio of the air/fuel mixture.

Attempts are being made to maximize the performance of combustors in addition to fuel economy improvements and emissions reduction by means of performing feedback control to attain a desired A/F ratio that is adaptive to a specific state of operation of the combustor. This goal, however, is not attained by the aforementioned oxygen sensor, which is merely capable of detecting the stoichiometric A/F ratio of the air/fuel mixture.

A sensor or analyzer capable of performing the above described A/F ratio feedback control has recently been proposed in Unexamined Published Japanese Patent Application Nos. 72286/1977 and 66292/1978; this device is provided with a chamber that forms a closed space including the surface of one of the two electrodes formed on a solid electrolyte and a small diffusion aperture is formed in the wall of this chamber; a voltage is applied across the two electrodes so that a gas component in the gas to be analyzed will be introduced into the chamber by diffusion; and the amount of current flowing through said solid electrolyte is measured to determine the concentration of the particular gas component.

In the device described above, the atmosphere around one of the two electrodes formed on a solid electrolyte provides a closed space that communicates with the atmosphere of the gas to be analyzed by means of a small diffusion limiting aperture. One major problem with this device is that the diffusion limiting means is difficult to fabricate since the diffusion limited current value must be measured in order to determine the concentration of a particular gas being monitored in the gas to be analyzed.

SUMMARY OF THE INVENTION

In order to solve the aforementioned problem, the present invention provides a novel A/F ratio sensor comprising an oxygen concentration electrochemical cell and an oxygen pump disposed in a face-to-face relationship with a gap being formed therebetween, the side of said electrochemical cell opposite the side facing said oxygen pump being in contact with the atmosphere, said gap forming a gas diffusion compartment that communicates with a gas of interest by way of a gas limiting means, wherein the gap existing between said oxygen concentration electrochemical cell and said oxygen pump has a width of no more than 0.2 mm and no less than 0.01 mm.

DESCRIPTION OF THE PREFERRED EMBODIMENTS

Each of the oxygen concentration electrochemical cell and the oxygen pump is formed on a solid electrolyte plate, such as a solid solution of $Y_2O_3$—$ZrO_2$, provided with a porous electrode on both sides thereof.

A typical example of the material of the solid electrolyte plate is a solid solution of zirconia and yttria or calcia. Other usable materials include solid solutions of cerium dioxide, thorium dioxide, and hafnium dioxide, a solid solution of a perovskite type oxide, and a solid solution of a trivalent metal oxide.

The porous electrode may be formed from platinum or gold by various methods; in one method, a powder of a suitable material selected from the above listed metals that is used as the principal component is formed into a paste, and the paste is printed in a predetermined pattern on the solid electrolyte by a thick-film deposition technique, followed by sintering of the printed coat; in another method, the powder of the starting material is applied onto the solid electrolyte by a suitable thin-film depositing technique such as flame spraying, chemical plating or evaporation.

If desired, two solid electrolyte plates may be provided; an oxygen concentration electrochemical cell and an oxygen pump are formed on opposite sides of one solid electrolyte plate, and another oxygen pump is formed on the other solid electrolyte plate. This arrangement is advantageous in that the oxygen pump will have an improved ability to let oxygen gas in and out of the diffusion compartment described later in this specification, thereby providing easier control of the oxygen partial pressure in the vicinity of the electrodes on the oxygen concentration electrochemical cell. It is, however, preferable for the purpose of the present invention that the greater part of one major surface of the diffusion compartment should be assumed by an electrode on the oxygen pump. It should also be noted that the area of the electrodes on the oxygen pump is preferred to be no smaller than 5 mm$^2$.

An atmosphere-introducing channel should be provided by a known method on at least the surface of the oxygen concentration electrochemical cell that does not face the diffusion compartment. This channel may be provided by joining a channel former composed of a U-shaped stress relaxing layer and a tabular support to the surface of a solid electrolyte that does not face the diffusion compartment.

The gas diffusion limiting means may be provided by one or more apertures that establish communication between the diffusion compartment and the atmosphere of the gas to be analyzed. Such apertures are preferably filled with a porous material so as to provide an increased resistance to gas diffusion.

Figure 5:
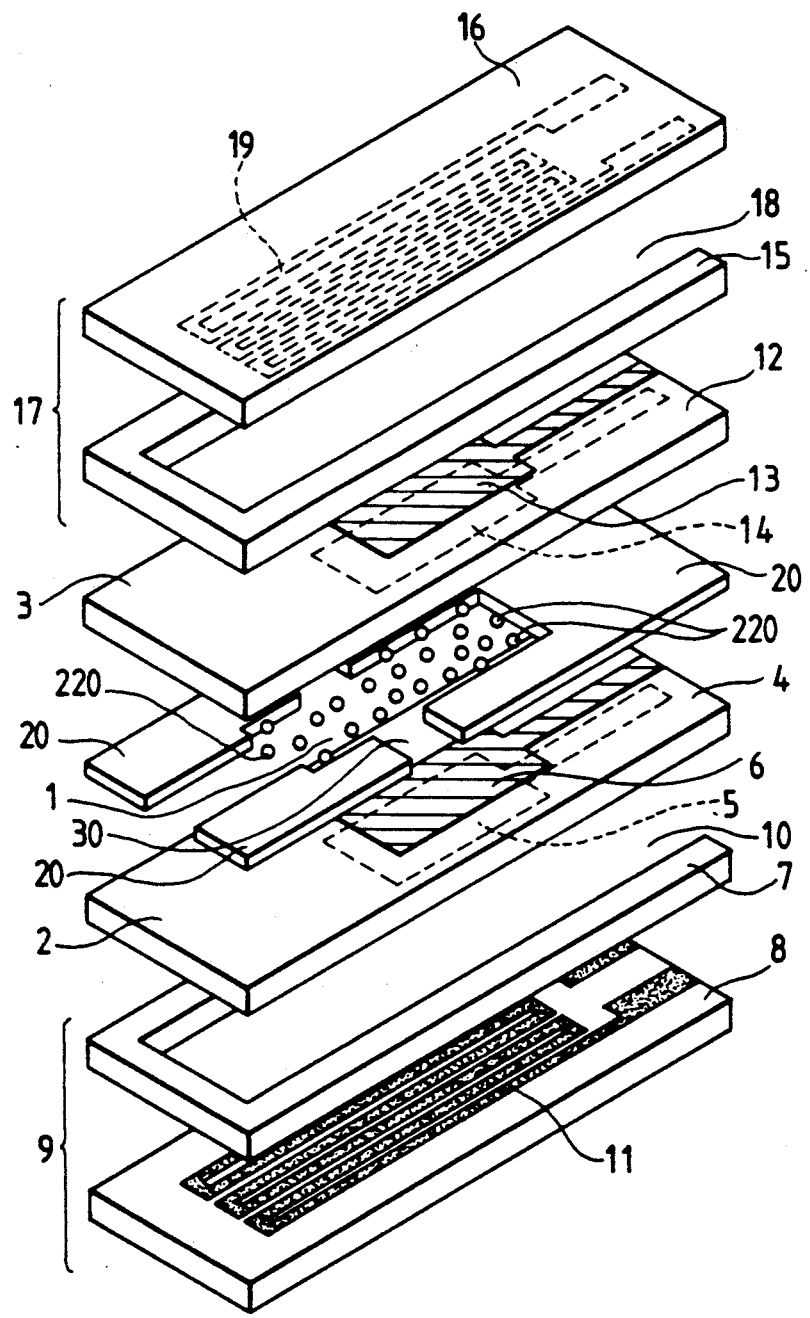
FIGS. 5 and 6 are illustrations similar to FIGS. 2 and 1, respectively, but showing the use of particles to prevent deformation of the diffusion compartment.
Figure 6:
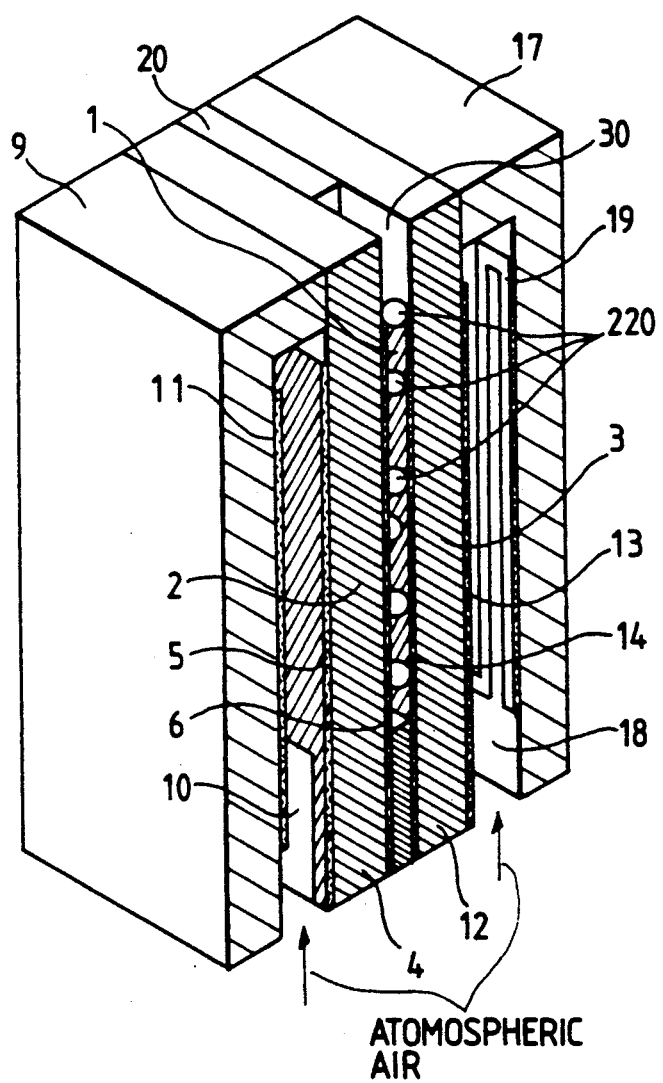

The diffusion compartment is formed by joining a solid electrolyte plate for the oxygen concentration electrochemical cell to another solid electrolyte plate for the oxygen pump, with a spacer having a cavity that forms part of the diffusion compartment being interposed between the two solid electrolyte plates. Prior to sintering, a single layer of granulated particles prepared from a spray dryer having a diameter approximately equal to the width of the diffusion compartment may be placed in said compartment as shown in the illustrations of FIGS. 5 and 6 wherein the particles are designated by reference numerals 220, and this is preferred for the purpose of preventing the diffusion compartment from deforming during the firing step.

The thickness of the diffusion compartment, or the distance between the opposing electrodes on the oxygen concentration electrochemical cell and the oxygen pump, is in the range of 0.01 to 0.2 mm, with the upper limit of 0.1 mm being preferred. If the thickness of the diffusion compartment is smaller than 0.01 mm, the compartment will limit the diffusion of oxygen gas so much as to decrease the response of the A/F ratio sensor. In addition, sensors of uniform quality cannot be fabricated since the thin diffusion compartment will easily deform during manufacture and presents considerable difficulty in ensuring the desired electrical insulation. If, on the other hand, the thickness of the diffusion compartment exceeds 0.2 mm, the differential pressure of the gas to be analyzed will change significantly within the diffusion compartment, and in particular, the differential pressure that exists between the opposing electrodes on the oxygen concentration electrochemical cell and the oxygen pump will be increased to cause not only an unduly great increase in the pumping current but also degraded response of the sensor. The increase in the differential pressure of the gas of interest that results from the use of an excessively thick diffusion compartment has been found to cause a problem even if the oxygen concentration electrochemical cell is designed to produce an output voltage of approximately 500 mV, typically 450 to 500 mV, when the sensor is operating for measurement purposes.

The operation of the A/F ratio sensor of the present invention described above will proceed as follows.

When the air/fuel mixture is in the lean region, the sensor is put into the exhaust gas and the electrode on the side of the oxygen pump which faces the atmosphere is supplied with a positive voltage while a negative voltage is applied to the electrode on the side facing the diffusion compartment. As a result, oxygen ions will move through the solid electrolyte of the oxygen pump toward the side opposite the diffusion compartment is pumped out of said compartment.

As the oxygen gas in the diffusion compartment is pumped out in the manner described above, a difference is produced between the concentration of oxygen on the side of the oxygen concentration electrochemical cell facing the atmosphere and the concentration of oxygen within the diffusion compartment, because of the oxygen diffusion limiting action of the diffusion limiting section. This differential oxygen concentration enables the oxygen concentration electrochemical cell to produce an electromotive force. If the amount of current flowing through the oxygen pump (pumping current) is adjusted such that the electromotive force E will be maintained at a predetermined level, a substantially linear relationship is obtained between the pumping current and the content of oxygen in the gas to be analyzed, thereby enabling the determination of the oxygen level of that gas.

When the air/fuel mixture is in the rich region, the oxygen concentration electrochemical cell of the oxygen sensor put into the exhaust gas will produce an electromotive force even if the oxygen pump is not actuated to create a differential oxygen partial pressure between the opposing electrodes. Therefore, in order to maintain the electromotive force from the oxygen concentration electrochemical cell at a constant value, the direction of the pumping current flowing through the oxygen pump should be reversed. More specifically, the oxygen at the electrode on the side of the oxygen concentration electrochemical cell facing the diffusion compartment is consumed by reaction with unburned hydrocarbons and carbon monoxide in the exhaust gas, and the differential oxygen partial pressure existing between the side of the cell facing the diffusion compartment and that of the cell which is in contact with the atmosphere is increased so much that the resulting electromotive force will exceed a predetermined level. As a result, in order to maintain the electromotive force at the predetermined value, oxygen must be pumped into the diffusion compartment by operating the oxygen pump. To this end, the pumping current is caused to flow in the direction opposite to that used when the air/fuel mixture is in the lean region. In addition, the amount of the required pumping current is proportional to the amounts of unburnt hydrocarbons and carbon monoxide in the exhaust gas. Therefore, the pumping current that is caused to flow in the rich region is also proportional to the A/F ratio of the air/fuel mixture.

Figure 3:
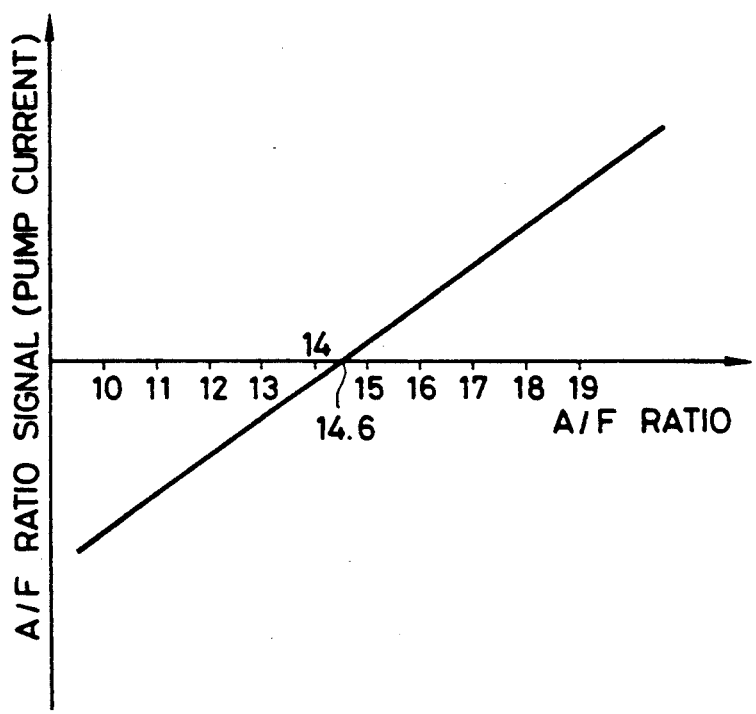
FIGS. 3 and 4 show the operating characteristics of the same sensor.

To summarize the foregoing explanation, if the pumping current that is caused to flow through the oxygen pump in the A/F ratio sensor of the present invention is adjusted so that the electromotive force generated by the oxygen concentration electrochemical cell will be maintained at a predetermined level, the resulting pump current will be proportional to the A/F ratio of the air/fuel mixture being sensed. This linear relationship is shown in FIG. 3.

The A/F ratio may also be determined from the electromotive force that is attained when the pumping current is maintained at a constant level. The relationship explaining this possibility may be best understood by reference to FIG. 4, wherein the direction of pumping current is assumed to be positive when oxygen is pumped out of the diffusion compartment.

When the pumping current $I_p$ is zero, the electromotive force makes an abrupt change at an A/F ratio that is substantially equal to the stoichiometric value (A/F=14.6). When the pumping current $I_p$ is negative (i.e., when oxygen is fed into the diffusion compartment), the electromotive force will make an abrupt change in the rich region. If the pumping current $I_p$ is positive, the slope of the change in the electromotive force is less steep than in the case of $I_p=0$ or $I_p<0$, but it still makes an abrupt change in the lean region. In other words, the point at which the electromotive force makes an abrupt change shifts from the rich to lean region as the pump current $I_p$ increase from negative to positive values.

It is known that the A/F ratio sensor exhibits better response characteristics if the oxygen partial pressure in the diffusion compartment is at the lower end. In accordance with the present invention, the diffusion compartment is in a flat form and helps to provide an even better A/F sensor performance by forming a uniform distribution in terms of the partial pressure of the gas to be analyzed within the diffusion compartment (i.e., the distribution of partial pressure as between the opposing electrodes on the oxygen concentration electrochemical cell and the oxygen pump).

Figure 1:
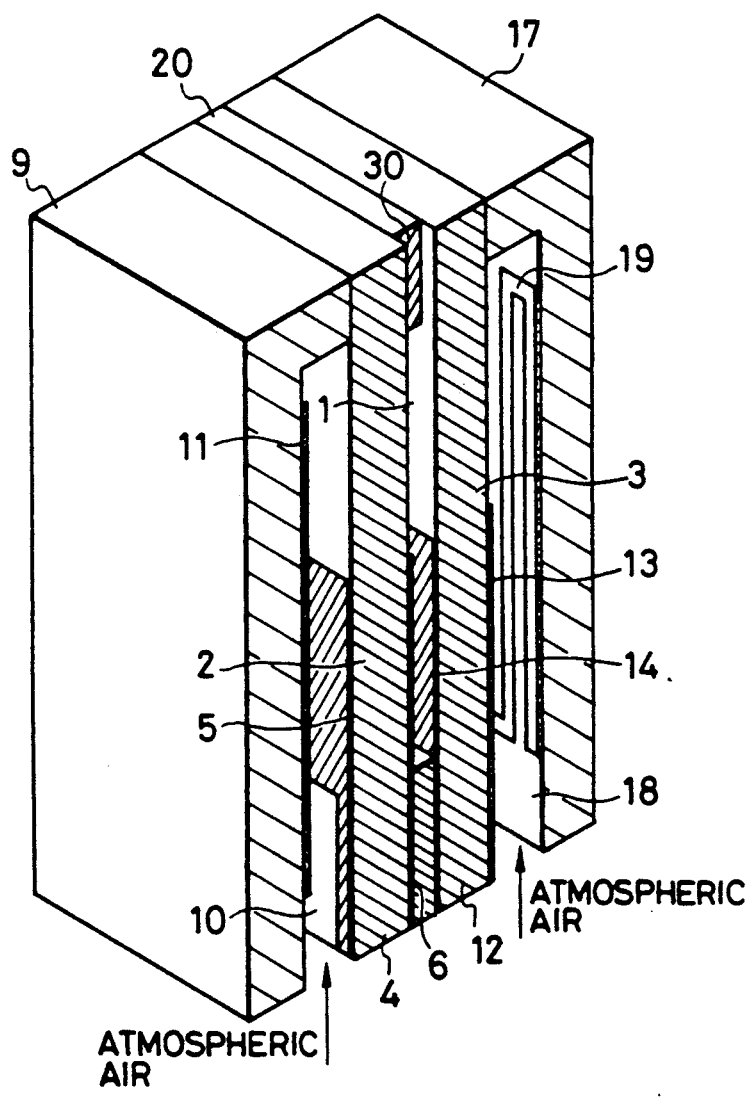
FIG. 1 is a partial fragmentary perspective view of the A/F ratio sensor in accordance with one embodiment of the present invention.
Figure 2:
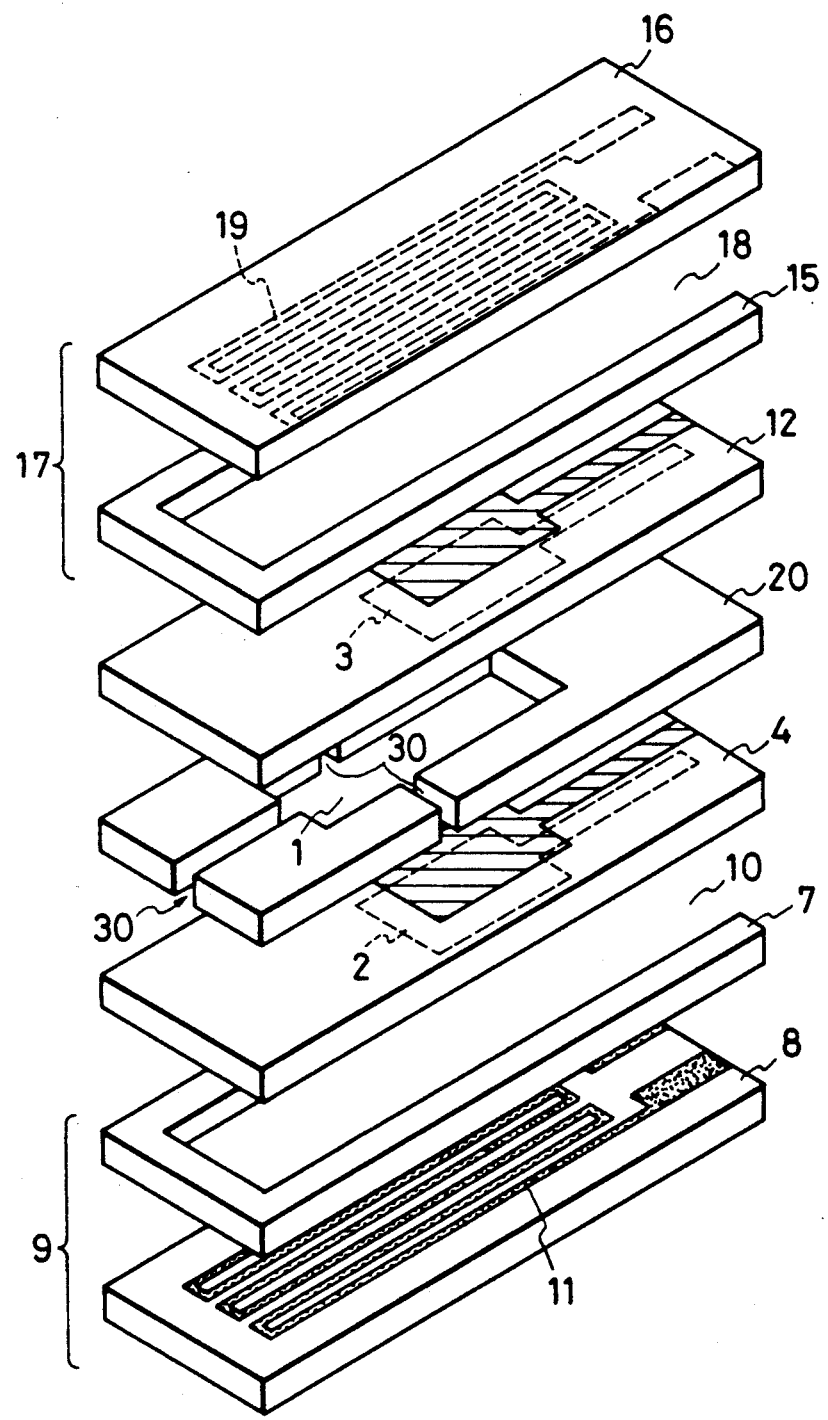
FIG. 2 is an exploded view of that sensor.

One embodiment of the A/F ratio sensor of the present invention is hereunder described with reference to FIGS. 1 and 2, which are a partial cutaway perspective view and an exploded view of the sensor, respectively.

The sensor of the embodiment shown is constructed so that a diffusion compartment 1 is formed between one oxygen concentration electrochemical cell 2 and one oxygen pump 3 that are disposed in a face-to-face relationship.

The oxygen concentration electrochemical cell 2 is composed of a solid electrolyte plate 4 ($7 \times 45 \times 0.6$ mm) that is made of an $Y_2O_3$-$ZrO_2$ solid solution and which has electrodes 5 and 6 formed on opposite sides of the plate by thick-film deposition of platinum containing 5 wt % of an $Y_2O_3$-$ZrO_2$ solid solution. The side of the solid electrolyte plate 4 that is opposite the side facing the diffusion compartment 1 is provided with a channel former 9 that is the combination of a U-shaped stress relaxing layer 7 (thickness, 1.0 mm; outer dimensions, $7 \times 45$ mm; inner dimensions, $5 \times 43$ mm) made of a sintered mixture of $Al_2O_3$ and $ZrO_2$ and an $Al_2O_3$ support ($7 \times 45 \times 0.8$ mm). Atmospheric air is introduced to make contact with the electrode 5 on the oxygen concentration electrochemical cell 2 through a channel 10 provided by the channel former 9. A heating element 11 is formed on the side of the support 8 facing the channel 10.

The oxygen pump 3 is similar to the oxygen concentration electrochemical cell 2 in that it is composed of a solid electrolyte plate 12, electrodes 12 and 13, and a channel former 17 comprises of a stress relaxing layer 15 and a support 16. Atmospheric air is introduced to make contact with the electrode 13 on the oxygen pump 3 through a channel 18 provided by the channel former 17. A heating element 19 is formed on the support 16.

The diffusion compartment 1 is formed by sandwiching a diffusion compartment/diffusion limiting section former 20 between the solid electrolyte plate 4 of the oxygen concentration electrochemical cell 2 and the solid electrolyte plate 12 of the oxygen pump 3. The member 20 is made of a sintered mixture of $Al_2O_3$ and $ZrO_2$, and has a generally U-shaped form (thickness, 0.1 mm; outer dimensions, $7 \times 45$ mm; inner dimensions, $3 \times 9$ mm) provided with a diffusion limiting section 30 ($0.1 \times 0.1$ mm in cross section) on three sides. The aperture of each diffusion limiting section may be filled with a porous material (typically made of bound alumina particles having a maximum porosity of 3 microns or less and an average porosity of 1.2 microns) so as to provide a greater diffusion resistance. The porous material used additionally to provide an increased resistance to gas diffusion may have a comparatively high porosity. Such a highly porous material is reasonably insensitive to clogging by dust particles, and hence has good resistance to deterioration of the performance of the sensor. In addition, the highly porous material is fairly easy to fabricate.

The diffusion compartment 1 in the A/F ratio sensor of the embodiment shown is in a flat form and the area of the electrodes on the oxygen pump 3 is sufficiently larger than the capacity of the diffusion compartment 1 to permit rapid diffusion limitation and reduce the differential partial pressure of the gas to be analyzed existing between the opposing electrodes on the oxygen concentration electrochemical cell and the oxygen pump, thereby ensuring good response characteristics and minimizing the required pumping current.

The stress relaxing layers 7 and 15 that are used in the channel formers 9 and 17, respectively, and each of which is made of a sintered mixture of $Al_2O_3$ and $ZrO_2$ are effective in preventing warpage of the A/F ratio sensor or its failure due to thermal expansion mismatch during service. It is to be noted that warpage of the sensor that may tend to occur during use can be substantially eliminated because it has a substantially symmetric configuration with respect to the plane of diffusion of compartment 1.

The heating elements 11 and 19 are advantageous in that they provide easy temperature compensation.

Figure 4:
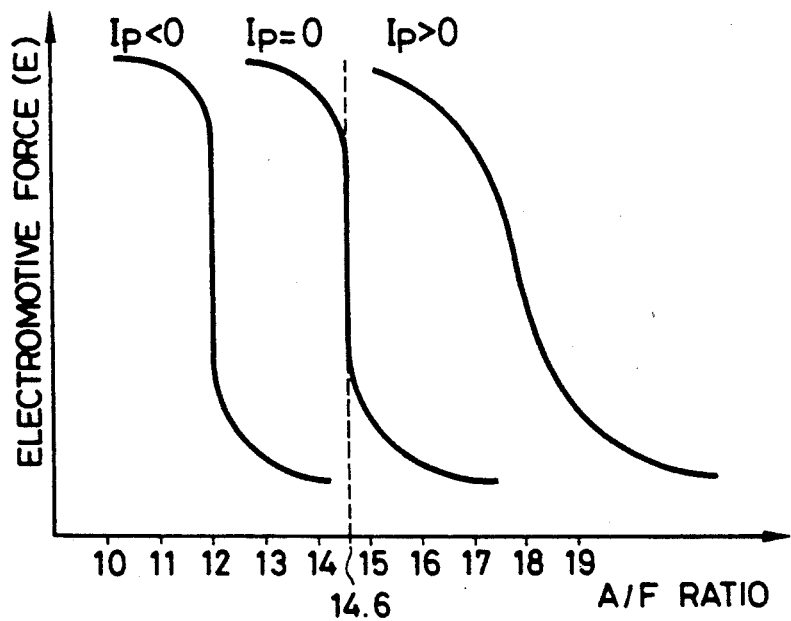

FIGS. 3 and 4 show the operating characteristics of the A/F ratio sensor of the present invention. As was noted above, FIG. 3 shows the pumping current vs. A/F ratio for a constant output voltage being produced from the oxygen concentration electrochemical cell 2, and FIG. 4 shows the relationship between the A/F ratio and the output voltage produced from the oxygen concentration electrochemical cell 2 when a constant pumping current is applied.

In the embodiment shown, an air-introducing channel is provided such that the electrode on that side of the oxygen pump which is opposite the side facing the gas diffusion compartment is exposed to the atmosphere. If desired, said side may be merel exposed to the exhaust gas so that oxygen may be picked up directly from the exhaust gas or indirectly from oxygen-containing components in the exhaust.

In accordance with the present invention, the diffusion compartment is in a flat form and has a gas diffusion limiting section at three points of its periphery. This permits the use of large electrodes for the oxygen pump in comparison with the capacity of the diffusion compartment. Any change in the partial pressure of the gas to be analyzed in the atmosphere in the diffusion chamber can be quickly cancelled to provide a uniform distribution in terms of the partial pressure between the opposing electrode, thereby enabling fabrication of an A/F ratio sensor having good response and high gas diffusion limiting efficiency. Particularly good results are obtained when the apertures formed in the periphery of the diffusion compartment are filled with a porous material.

The stress relaxing layer used in each of the channel formers has the advantage of preventing warpage of the A/F ratio sensor during use, and failure due to thermal expansion mismatch.

Since both of the oxygen concentration electrochemical cell and the oxygen pump are provided on a single solid electrolyte plate, the use of solid electrolytes is reduced to make contribution to the conservation of resources.

The operating range of the sensor can be expanded and its response improved by using a second oxygen pump.

In a preferred embodiment, a layer of particles may be placed in the diffusion compartment in a thickness equal to that of the latter; this is effective in preventing deformation of the diffusion compartment in fabrication procedures, especially in the firing step, thereby enabling mass production of acceptable sensors.

We claim:

1. An air/fuel ratio sensor, comprising:
   an oxygen concentration electrochemical cell;
   an oxygen pump disposed in face-to-face relationship with said oxygen concentration electrochemical cell to form a gap therebetween; and
   diffusion limiting means for enclosing a substantial portion of the periphery of said gap except for at least one aperture to thereby form a gas diffusion compartment which is surrounded by said diffusion limiting means and which communicates with a gas to be analyzed through said aperture; and
   a plurality of support members other than said diffusion limiting means disposed within said diffusion compartment, wherein said support member comprise granulated particles each having a diameter substantially the same as the width of said gap.

2. An air/fuel ratio sensor according to claim 1, wherein said support members comprise a single layer of said granulated particles so that each particle is substantially in contact with both sides of said gap. t

* * * * *